United States Patent [19]

Crawford

[11] 4,232,168
[45] Nov. 4, 1980

[54] PREPARATION OF ASCORBIC ACID INTERMEDIATES

[75] Inventor: Thomas C. Crawford, New London County, Conn.

[73] Assignee: Pfizer Inc., New York, N.Y.

[21] Appl. No.: 805,880

[22] Filed: Jun. 13, 1977

[51] Int. Cl.$^2$ .................. C07C 67/00; C07C 69/67; C07C 51/00; C07C 59/33
[52] U.S. Cl. .................. 560/174; 260/340.7; 260/343.7; 562/577
[58] Field of Search ............ 560/174; 260/528, 531 R, 260/340.7; 562/577

[56] References Cited

U.S. PATENT DOCUMENTS

| | | | |
|---|---|---|---|
| 2,207,991 | 7/1940 | Pasternack et al. | 560/174 |
| 2,847,421 | 8/1958 | D'Addieco | 562/537 |
| 4,111,958 | 9/1978 | Crawford | 260/340.7 |

OTHER PUBLICATIONS

Matsui et al., Yakugaku Zasshi 86, 110–113, (1966).
Meguro et al., Biol. Chem., vol. 36, No. 12, pp. 2075–2079.
Hulyakar et al., Can. J. Chem., vol. 41, pp. 1898–1904, (1963).
Chem. Abstracts, 40:1453', (1946).
Ogura et al., J. Org. Chem., vol. 37, No. 1, pp. 72–75, (1972).
Matsui et al., Chem. Pharm. Bull., 16(7), pp. 1288—1293, (1968).
Ness et al., J.A.C.S., 73, pp. 4759–4761, (1951).
Kohn et al., J.A.C.S., 87, pp. 5475–5480, (1965).
Upson et al., J.A.C.S., 58, pp. 2549–2552, (1936).
Kohn et al., J.A.C.S., 86, pp. 1457–1458, (1964).

*Primary Examiner*—Vivian Garner
*Attorney, Agent, or Firm*—Connolly and Hutz

[57] ABSTRACT

A synthetic route to ascorbic acid is provided in which a 3,5:4,6-protected derivative of gulonic acid is prepared from gulono-1,4-lactone. Oxidation of the derivative and hydrolysis of the resulting product affords 2-ketogulonic acid or ester thereof which can be readily converted to ascorbic acid by known methods.

6 Claims, No Drawings

PREPARATION OF ASCORBIC ACID INTERMEDIATES

BACKGROUND OF THE INVENTION

L-ascorbic acid, or vitamin C, is required in the human diet and is widely sold in tablet form and as an additive in various foodstuffs to meet this need. In all animals except primates and guinea pigs L-ascorbic acid is biosynthesized from D-glucose. The final step in this biosynthesis is the enzymatic conversion of L-gulono-1,4-lactone to L-ascorbic acid. British Pat. No. 763,055 discloses the conversion of L-gulono-1,4-lactone to L-ascorbic acid in about 40% yield by the use of an enzymatic oxidation system.

L-ascorbic acid and some of its derivatives are employed as antioxidants in foodstuffs to prevent rancidity, to prevent browning of cut fruit and in meat curing. D-ascorbic acid may also be used.

Attempts to effect the direct conversion of gulono-1,4-lactone to ascorbic acid by chemical means have only partly been successful since over-oxidation and degradation reactions product undesirable by-products. However, low yields of L-ascorbic acid have been produced by oxidation. For example, Berends and Konings, Rec. Trav. Chim. des Pays-Bas, 74, 1365 (1955), disclose the use of Fenton's reagent to give a 10% yield of L-ascorbic acid. The most successful and common method of producing L-ascorbic acid is based on a multi-step synthesis from D-glucose going through sorbose and 2-ketogulonic acid as described by Reichstein and Grussner, Helv. Chim. Acta., 17, 311 (1934).

U.S. Pat. No. 2,847,421 discloses a process for the production of intermediates 3,5:4,6-diethylidene-L-gulonic acid and its simple esters and salts in the synthesis of ascorbic acid from D-sorbitol. However, the yields are not very satisfactory.

SUMMARY OF THE INVENTION

This invention is concerned with a process for preparing 2-ketogulonic acid or esters thereof. The starting material, gulono-1,4-lactone, is reacted with a diallkyl aldehyde acetal or an aldehyde and an alkanol to provide a 3,5:4,6-protected derivative of gulonic acid. Oxidation affords the ester of xylo-hexulosonic acid. Hydrolysis yields 2-ketogulonic acid or ester or ascorbic acid.

DETAILED DESCRIPTION OF THE INVENTION

In the process of the present invention, a 3,5:4,6-protected derivative of L-gulonic acid (II) is prepared from L-gulono-1,4-lactone (I). Oxidation yields the L-xylo-hexulosonate (III) which on hydrolysis affords 2-keto-L-gulonic acid or its ester (IV) or directly affords L-ascorbic acid. The synthetic scheme is represented as follows:

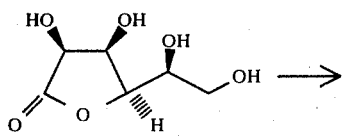

I

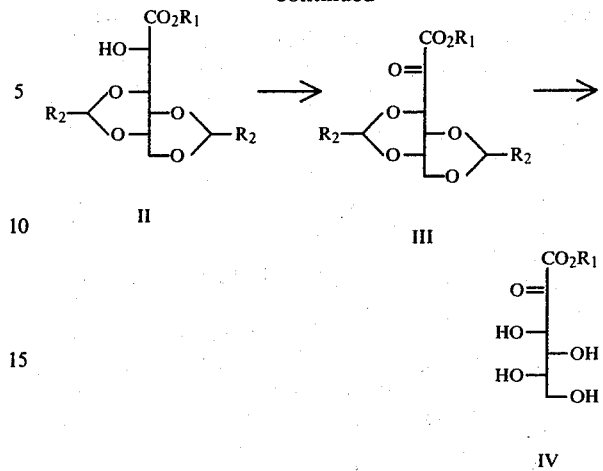

wherein $R_1$ is alkyl of 1 to 6 carbon atoms and $R_2$ is alkyl having 1 to 6 carbon atoms, phenyl, monosubstituted or disubstituted phenyl wherein the substituents are alkyl having 1 to 6 carbon atoms, alkoxy having 1 to 6 carbon atoms, chloro, bromo, fluoro or nitro.

It is to be understood that the process of the present invention is also applicable for the preparation of intermediates for the synthesis of D-ascorbic acid starting with D-gulono-1,4-lactone in place of L-gulono-1,4-lactone. D-gulono-1,4-lactone can be prepared from D-xylose by the process described in Organic Syntheses IV, 506 (1963).

The first step in the present process is the formation of a 3,5:4,6-protected intermediate. This may be effected by contacting the appropriate gulono-1,4-lactone with about two equivalents of an alkyl or aryl aldehyde of the formula $R_2CHO$. The preferred alkyl aldehyde is acetaldehyde and the preferred aryl aldehyde is benzaldehyde. The reaction is conducted in the presence of about one equivalent of an alcohol of 1 to 6 carbon atoms of the formula $R_1OH$. A modest excess of alcohol may be used with the excess considered a solvent or diluent. The preferred alcohols are methanol, ethanol, propanol or isopropanol. A catalytic amount of an acid having a $pK_a$ less than 3 is generally added in an amount between about 0.05 and 1.5 moles per mole of gulono-1,4-lactone. Suitable acid catalysts include, but are not limited to, hydrochloric acid, hydrobromic acid, hydrofluoric acid, sulfuric acid, p-toluenesulfonic acid and sulfonic ion exchange resins. The reaction may be conducted at 0°-70° C., preferably 20°-30° C., until the reaction is substantially complete (1-20 hours). Alternatively, the gulono-1,4-lactone is contacted with two equivalents of the appropriate aldehyde dialkyl acetal of the formula $R_2CH(OR_1)_2$ in the absence of an accompanying alcohol.

The second step in the present process is the oxidation of the unprotected hydroxy group at the 2-position of the protected lactone to keto. This may be effected by any method known in the art for the oxidation of secondary alcohols to ketones. A preferred oxidizing agent is a sulfoxonium salt formed from a mixture of dimethyl sulfoxide and, for example, acetic anhydride or trifluoroacetic anhydride in the presence of a base such as triethylamine. A useful chemical combination is potassium periodate and ruthenium dioxide in the presence of a base such as potassium carbonate. The oxidation is conducted in an organic solvent inert to oxidation conditions. Examples of suitable solvents include, but are not limited to, dimethyl formamide, pyridine, dimethyl sulfoxide, dichloromethane and acetone. It is not necessary that the intermediate be fully soluble in the organic medium. Temperatures suitable for the oxidation reaction will vary according to the type of oxidation employed.

For example, in oxidation via sulfoxonium salts, the oxidation may e conducted at −60° to about 100° C. depending on the method used to generate the sulfoxonium salts. The very low temperature is required only when trifluoroacetic anhydride is used to generate the initial sulfoxonium salt. The reaction is preferably carried out at 0° to 50° C. Oxidation by potassium periodate and ruthenium dioxide is conducted at about −10° C. to about 50° C., preferably about 0° C. to room temperature. Before proceeding to the next step of the process the oxidized intermediate is preferably separated from any excess oxidizing agent, for example, by filtration of solid catalyst residues or by extraction or recrystallization of the product.

The oxidation process may also be accomplished by first contacting the di-O-alkylidene or arylidene-gulonate at about −20° C. with acetic anhydride and nitric acid to form the 2-nitrato-gulonate. The isolated product in a solvent such as diethyl ether at 0°–5° C. is stirred for about 15 minutes following the addition of triethylamine. The resulting homogeneous solution following the addition of dichloromethane is further stirred at 0°–5° C. and then worked up to yield the xylo-hexulosonate.

The final step in the process is the hydrolysis of the xylohexulsonate to the 2-ketogulonic acid ester. Temperatures in the range of about 35° to 150° C. are suitable with temperatures of about 50° to 75° C. being preferred. The choice of solvent-acid mixture is not critical with examples of useful mixtures as follows:
- water-methanol, Amberlite IR-120 sulfonic acid exchange resin
- isopropanol-water, catalytic amount of concentrated sulfuric acid
- acetonitrile-methanol, Dowex 50-X8 sulfonic acid exchange resin
- water-acetic acid
- ethylene glycol-tetrahydrofuran, methanesulfonic acid The 2-ketogulonic acid ester can be hydrolyzed to the free acid or it can be converted by further reaction to ascorbic acid. Alternatively, the alkyl 3,5:4,6-di-O-protected xylo-hexulsonate can be converted to ascrobic acid under acid catalyzed hydrolysis conditions which are known to convert 2-ketogulonic acid, methyl 2-ketogulonate or diacetone-2-ketogulonic acid or ester to ascorbic acid.

EXAMPLE I

Methyl 3,5:4,6-Di-O-benzylidene-L-gulonate

To 11.2 ml (113 mmol) of benzaldehyde and 2.3 ml (57 mmol) of methanol was added 5.04 g (28.3 mmol) of L-gulono-1,4-lactone followed by 1.12 ml (13.4 mmol) of concentrated hydrochloric acid. On stirring for 20 hrs at room temperature the initially mobile slurry turned solid. The reaction mixture was triturated with ether and filtered. The solids were washed with ether, two times with water, and then ether. After drying in vacuo, the white solid weighed 6.2 g (16.1 mmol, 57%; based on unrecovered gulonolactone, 82%), mp 177°–180°. Recrystallization from benzene—acetone afforded analytically pure material, mp 180°–183°: $[\alpha]_D^{23}+64.5°$ (DMF); ir (KBr) 3340, 1733 cm$^{-1}$; nmr (DMSO-d$_6$) $\delta_H$3.65 (s, 3, —OCH$_3$), 3.86–4.53 (m, 6), 5.66 (s, 2, —OCHO—), 6.10 (d, 1, J=5, —OH), 7.2–7.63 (m, 10, aromatic); ms 386 (1.9), 385 (5.2), 297 (13.1), 149 (25.9), 107 (40.6), 106 (21.7), 105 (100), 91 (57.8), 79 (26.5), 78 (10.7), 77 (38.9).

Anal. Calcd for $C_{21}H_{22}O_7$: C, 65.27; H, 5.74. Found: C, 65.22, H, 5.74.

EXAMPLE II

The method of Example I may be repeated replacing benzaldehyde with each of the following aldehydes:

| | |
|---|---|
| acetaldehyde | o-methylbenzaldehyde |
| propionaldehyde | m-methylbenzaldehyde |
| n-valeraldehyde | 3,4-dichlorobenzaldehyde |
| n-hexaldehyde | o-methoxybenzaldehyde |
| o-nitrobenzaldehyde | o-chlorobenzaldehyde |
| o-fluorobenzaldehyde | o-butoxybenzaldehyde |
| m-bromobenzaldehyde | o-hexoxybenzaldehyde |

EXAMPLE III

Ethyl 3,5:4,6-Di-O-benzylidene-L-gulonate

To a 250-ml flask under nitrogen was added 10.1 g (56.7 mmol) of L-gulono-1,4-lactone, 44 g (244 mmol) of benzaldehyde diethyl acetal, and 2.5 ml (30 mmol) of concentrated hydrochloric acid. The reaction was initially exothermic. After 2 hrs the reaction was solid and this solid mixture stood at room temperature for 17 hrs. The reaction was worked up by triturating with 100 ml of ether three times, water two times, and ether two times. After drying under vacuum, the resulting crystalline solid weighed 21.0 g (52.5 mmol, 92.6%) which was pure by tlc. This material was recrystallized from 500 ml of chloroform and 200 ml of diisopropyl ether. The first crop of crystals weighed 16.7 g (41.7 mmol, 74%) and the second crop of crystals weighed 2.3 g (5.7 mmol, 10%), mp 203°–204°: $[\alpha]_D^{23}+61.2°$ (DMF); ir (KBr) 3330, 1724 cm$^{-1}$; nmr (DMSO-d$_6$) $\delta_H$1.13 (t, 3, J=6.5, —CH$_3$), 4.07 (m, 8), 5.68 (s, 2, —OCHO—), 6.03 (d, 1, J=5, —OH), 7.40 (s, 10, aromatic); nmr (DMSO-d$_6$) $\delta_C$ 172.2 (1, s, —CO$_2$—), 138.4, 138.0 (2, s, aromatic), 128.6, 127.9, 126.0, 125.9, (6, —CH—, aromatic), 99.4, 99.1 (2, d, —OCHO—), 78.4 69.83, 67.8 (4, each a d, —OCH—), 69.79 (1, t, —CH$_2$O—), 60.1 (1, t, —OC$\underline{H}_2$CH$_3$), 14.2 (1, q, —CH$_3$); ms 400 (0.8), 297 (10.1), 149 (20.7), 107 (33.3), 106 (28.4), 105 (100), 91 (45.0), 81 (10.6), 79 (18.2), 77 (38.6), 51 (13.1), 44 (10.6), 43 (10.2).

Anal. Calcd for $C_{22}H_{24}O_7$: C, 66.06; H, 6.05. Found: C, 65.97; H, 6.03.

EXAMPLE IV

The method of Example III may be repeated replacing benzaldehyde diethyl acetal with each of the following aldehyde dialkyl acetals:
  acetaldehyde diethyl acetal
  acetaldehyde dimethyl acetal
  propionaldehyde dipropyl acetal
  n-valeraldehyde dimethyl acetal
  n-hexaldehyde dibutyl acetal
  o-nitrobenzaldehyde dihexyl acetal
  o-fluorobenzaldehyde diethyl acetal
  o-bromobenzaldehyde diethyl acetal
  o-methylbenzaldehyde dimethyl acetal m-methylbenzaldehyde dipropyl acetal
3,4-dichlorobenzaldehyde diethyl acetal
o-chlorobenzaldehyde diethyl acetal
o-methoxybenzaldehyde diethyl acetal
o-chlorobenzaldehyde diethyl acetal
o-butoxybenzaldehyde dimethyl acetal
o-hexoxybenzaldehyde diethyl acetal

EXAMPLE V

Ethyl 3,5:4,6-Di-O-benzylidene-L-gulonate from 3,5-O-Benzylidene-L-gulono-1,4-lactone To 0.266 g (1.0 mmol) of 3,5-O-benzylidene-L-gulono-1,4-lactone was added 0.360 g (2.0 mmol) of benzaldehyde diethyl acetal and approximately 40 µl of concentrated hydrochloric acid. After 0.5 hour, the reaction mixture became very thick and stirring stopped. After standing at room temperature for 20 hours, the solid was triturated with diethyl ether and filtered. The resulting solid after drying weighed 0.257 g (0.64 mmol, 64%). Recrystallization from benzene containing a small amount of acetone afforded a white crystalline solid, mp 204°-205° C. which was identical with the material prepared in Example III.

EXAMPLE VI

Ethyl 3,5:4,6-Di-O-benzylidene-L-gulonate from Benzaldehyde and Ethanol

To 11.2 ml (113 mmol) of benzaldehyde and 1.63 ml (28.3 mmol) of ethanol was added 5.04 g (28.3 mmol) of L-gulono-1,4-lactone followed by 1.12 ml (13.4 mmol) of concentrated hydrochloric acid. The reaction mixture was initially a mobile slurry which turned solid on stirring at room temperature for 20 hrs. The reaction mixture was triturated with ether and then filtered. The solid was washed with ether and then two times with water. After drying, this white crystalline solid weighed 2.92 g (7.3 mmol, 26%). Based on unrecovered gulonolactone the yield was 47%. This material was identical with that prepared in Example III.

EXAMPLE VII

Ethyl 3,5:4,6-Di-O-benzylidene-L-gulonate from 3,5-O-Benzylidene-L-gulono-1,4-lactone To 2 ml of dimethylformamide was added 1.33 g (5.0 mmol) of 3,5-O-benzylidene-L-gulono-1,4-lactone followed by 0.946 g (5.25 mmol) of benzaldehyde diethyl acetal and a catalytic amount of toluenesulfonic acid. After stirring at room temperature for 2 hrs, sodium bicarbonate was added, the solution was filtered, tetrahydrofuran was added, the solution was washed with brine, dried with sodium sulfate, and concentrated in vacuo affording 1.359 g (3.40 mmol, 68%) of a white solid. This material was identical with material prepared in Example III.

EXAMPLE VIII

Isopropyl 3,5:4,6-Di-O-benzylidene-L-gulonate

To a solution of 40.4 ml (0.40 mol) of benzaldehyde and 38.2 ml of isopropanol was added 8.9 g (0.050 mol) of L-gulono-1,4-lactone followed by 2.0 ml (0.024 mol) of concentrated hydrochloric acid. The reaction mixture was stirred at room temperature for 30 min at which time 0.10 g of seed crystals was added. This solution was stirred at room temperature for 72 hrs. It was then triturated with ether, filtered, and the solids were washed three times with ether, three times with water, and two times with ether. After drying under vacuum, 7.67 g (18.5 mmol, 37%) of a white solid was recovered. The yield based on unrecovered L-gulono-1,4-lactone was 49%. Analytically pure material was obtained by recrystallization from ethyl acetate, mp 183°-186°: ir (KBr) 3356, 1715 cm$^{-1}$; nmr (DMSO-d$_6$) $\delta_H$ 1.07 and 1.15 (two d, 6, J=7, —CH$_3$), 3.97-4.40 (m, 6), 4.97 (heptet, 1, J=7, —OCH(CH$_3$)$_2$), 5.73 (s, 2, —O-CHO—), 6.06 (m, 1, —OH), 7.47 (s, 10, aromatic); ms 414 (0.6), 413 (3.4), 297 (16.6), 149 (28.5), 107 (38.0), 106 (20.9), 105 (100), 91 (42.0), 77 (25.3), 44 (16.4), 43 (11.0).

Anal. Calcd for C$_{23}$H$_{26}$O$_7$: C, 66.65; H, 6.32. Found: C, 66.51, H, 6.25.

EXAMPLE IX

Methyl 3,5:4,6-Di-O-ethylidene-L-gulonate

To 5.0 g (28.1 mmol) of L-gulono-1,4-lactone was added 12.2 ml (112.3 mmol) of acetaldehyde dimethyl acetal. Hydrogen chloride gas was bubbled through the heterogeneous solution. The reaction mixture gradually became homogeneous and was stirred at room temperature for 20 hrs. The reaction mixture was concentrated and the resulting solid was triturated with ether affording 3.67 g (14.0 mmol, 50%) of material. In addition, the ether filtrate afforded 2.93 g (11.2 mmol, 40%) of solid which by tlc was pure material. The triturated solid was recrystallized from chloroform and then ethyl acetate to afford analytically pure material, mp 137°-140° (lit.* 144°-145.5°): [α]$_D^{27}$+20.5° (DMF); ir (KBr) 3436, 1748 cm$^{-1}$; nmr (DMSO-d$_6$) $\delta_H$ 1.20 (d, 3, J=5, —CH$_3$), 1.25 (d, 3, J=5, —CH$_3$), 3.67 (s, 3, —OCH$_3$), 3.72-4.33 (m, 6), 4.77 (q, 2, J=5, —CHCH$_3$), 5.22 (d, 1, J=6, —OH); nmr (DMSO-d$_6$) $\delta_C$ 172.7 (s, —CO$_2$—), 97.60 (d, —O-CHO—), 97.55 (d, —OCHO—), 78.0, 69.1, 67.5, 67.0 (d, —CO—), 68.7 (t, —CH$_2$O—), 51.4 (q, —OCH$_3$), 20.9 (q, —CH$_3$), 20.7 (q, —CH$_3$); exact mass (C$_{11}$H$_{18}$O$_7$-H), 261.0988 (calcd 261.1002).

*A. A. D'Addieco, U.S. Pat. No. 2,847,421 (1958).

Anal. Calcd for C$_{11}$H$_{18}$O$_7$: C, 50.37; H, 6.91. Found: C, 50.63; H, 6.86.

EXAMPLE X

The methods of Examples I to IX may be repeated replacing L-gulono-1,4-lactone with D-gulono-1,4-lactone to obtain the the corresponding D-gulonates.

EXAMPLE XI

Ethyl 3,5:4,6-Di-O-benzylidene-L-xylo-hexulosonate

To a dry 250-ml 3-neck flask under nitrogen was added 30 ml of dry dichloromethane. To this was added at −60° 1.4 ml (10 mmol) of trifluoroacetic anhydride followed by 10 mmol (0.71 ml) of dry dimethylsulfoxide. This solution was stirred at −60° or lower for 30 min and then 2.00 g (5.0 mmol) of ethyl 3,5:4,6-di-O-benzylidene-L-gulonate in 30 ml of dry dichloromethane was added over a 10 min period while maintaining the temperature below −45°. The resulting solution was stirred at less than −60° for 30 min, then 2 ml (14.4 mmol) of triethylamine was added. After 20 min at less than −60°, the solution was allowed to warm to room temperature and stirred for 2.25 hrs. An additional 40 ml of dichloromethane was added to the reaction mixture which was then extracted two times with 50 ml of 1 N hydrochloric acid, two times with 50 ml of water, one time with 50 ml of brine and dried with sodium sulfate. Removal of the solvent in vacuo afforded 1.94 g (4.9 mmol, 98%) of an off-white solid which was one spot by tlc. Recrystallization from benzene—acetone afforded analytically pure material, mp 192°–194°. This material can also be recrystallized from chloroform—diisopropyl ether: $[\alpha]_D^{23}+10.4°$ (DMF); ir (KBr) 1754, 1733 cm$^{-1}$; nmr (DMSO-d$_6$) $\delta_H$ 1.27 (t, 3, J=7, —CH$_3$), 4.27 (m, 5), 4.78 (m, 1), 5.53 (d, 1, J=2, —COCHO), 5.72 (s, 1, —OCHO—), 5.88 (s, 1, —OCHO—), 7.40 (m, 10, aromatic); nmr (DMSO-d$_6$) $\delta_C$ 188.0 (1, CO), 159.8 (1, —CO$_2$—), 137.8, 137.6 (2, C, aromatic), 128.9, 128.6, 128.0, 126.2, 125.7 (10, —CH, aromatic), 99.1, 98.6 (2, —OCHO—), 80.3, 69.8, 69.0, 68.8 (4), 62.2 (1, —OCH$_2$CH$_3$), 13.9 (1, —CH$_3$); ms 397 (0.1), 396 (0.6), 298 (13.8), 297 (69.8), 191 (14.9), 149 (10.6), 107 (36.7), 106 (23.1), 105 (94.8), 91 (100), 85 (41.5), 79 (28.4), 78 (10.0), 77 (39.7), 57 (10.4), 51 (11.5).

Anal. Calcd for C$_{22}$H$_{22}$O$_7$: C, 66.32; H, 5.56. Found: C, 66.29; H, 5.69.

EXAMPLE XII

Ethyl 3,5:4,6-Di-O-benzylidene-L-xylo-hexulosonate

To a dry 1—l 3-neck flask under nitrogen was added 100 ml of dry dichloromethane followed by 4.3 ml (4.73 g, 60.6 mmol) of dry dimethyl sulfoxide. This solution was cooled to −60° and 8.5 ml (60.0 mmol) of trifluoroacetic anhydride was added while maintaining the reaction temperature below −55°. After 30 min at −60° or less, 290 ml of dichloromethane containing 12.0 g (30.0 mmol) of ethyl 3,5:4,6-di-O-benzylidene-L-gulonate was added over a 45 min period. The reaction temperature was kept below −50°. The reaction was stirred for an additional 30 min at −55° and then 12.6 ml (90 mmol) of triethylamine was added. After 30 min at −55°, the solution was stirred at room temperature for 2 hrs. An additional 200 ml of dichloromethane was added and the reaction mixture was extracted two times with 300 ml of 1 N hydrochloric acid, two times with 300 ml of water, and two times with 300 ml of brine. After drying the organic layer with sodium sulfate, the solvent was removed in vacuo affording 11.78 g (29.6 mmol, 98.7%) of a white solid which was identical with material prepared in Example XI.

This oxidation can also be carried out using dimethylsulfoxide and acetic anhydride.

EXAMPLE XIII

Ethyl 3,5:4,6-Di-O-benzylidene-L-xylo-hexulosonate

To a 35-ml flask was added 7 ml of dichloromethane and 0.40 g (1.0 mmol) of ethyl 3,5:4,6-di-O-benzylidene-L-gulonate followed by 33 mg (0.24 mmol) of potassium carbonate, 0.299 g (1.30 mmol) of potassium periodate, and 7 mg of ruthenium dioxide. After 6 hrs, an additional 33 mg (0.24 mmol) of potassium carbonate, 0.299 g (1.30 mmol) of potassium periodate, and 7 mg of ruthenium dioxide was added. The reaction mixture was stirred for 18 hrs and then diluted with dichloromethane, extracted two times with water, two times with brine, and dried with sodium sulfate. Concentration in vacuo afforded a white solid (0.328 g, 0.82 mmol, 82%) which was recrystallized from ethyl acetate. This afforded 0.188 g (0.47 mmol, 47%) of white needles, mp 195°–198°. This material was identical with material prepared in Example XI.

EXAMPLE XIV

Isopropyl 3,5:4,6-Di-O-benzylidene-L-xylo-hexulosonate

To a dry 50-ml 3-neck flask under nitrogen was added 12 ml of dry dichloromethane and 0.85 ml (6 mmol) of trifluoroacetic anhydride. This solution was cooled to −60° and 0.43 ml (6 mmol) of dimethylsulfoxide was added. After stirring for 30 min, 17 ml of dichloromethane containing 1.24 g (3.0 mmol) of ispropyl 3,5:4,6-di-O-benzylidene-L-gulonate was added to the reaction mixture while maintaining the temperature below −50°. After 30 min at −55° or lower, 1.26 ml (9 mmol) of triethylamine was added. The resulting solution was stirred at −55° for 45 min and then at room temperature for 2.5 hrs. The reaction was worked up by adding dichloromethane and extracting two times with 1 N hydrochloric acid, three times with water, and once with brine. After drying with sodium sulfate, the solvent was removed in vacuo affording 1.29 g (3.15 mmol, 104%) of a white solid. Recrystallization from chloroform—isopropyl ether afforded 0.649 g (1.58 mmol, 52.5%) of analytically pure white needles, mp 188°–191°: (KBr) 1754, 1739 cm$^{-1}$; nmr (DMSO-d$_6$) $\delta_H$ 1.23 and 1.30 (two d, 6, J=6, —CH$_3$), 4.23 (m, 3), 4.73 (m, 1), 5.12 (heptet, 1, J=6, —CH(CH$_3$)$_2$), 5.50 (d, 1, J=3, —OCCHO—), 5.70 (s, 1, —OCHO—), 5.87 (s, 1, —OCHO—), 7.43 (m, 10, aromatic); ms 413 (0.1), 412 (0.3), 411 (1.7), 298 (16.4), 297 (76.9), 191 (20.1), 149 (19.7), 107 (61.0), 106 (20.9), 105 (86.4), 91 (100), 85 (35.9), 79 (17.2), 77 (18.5), 44 (10.1).

Anal. Calcd for C$_{23}$H$_{24}$O$_7$: C, 66.97; H, 5.86. Found: C, 66.10; H, 5.79.

EXAMPLE XV

Ethyl 3,5:4,6-Di-O-benzylidene-2-nitrato-L-gulonate

To a 25-ml 3-neck flask containing 5 ml of acetic anhydride at −20° was added dropwise 2 ml of nitric acid. This solution was then warmed to −10° at which point an exothermic reaction took place causing the temperature to rise to 5°. After cooling to −10°, 4.4 ml of this solution was added with stirring to a solution of 1.16 g (2.90 mmol) of ethyl 3,5:4,6-di-O-benzylidene-L-gulonate in 30 ml of dry dichloromethane and 2 ml of acetic anhydride at −15°. After 25 min the reaction mixture was poured onto 200 ml of ice—water. After stirring for 30 min, the reaction mixture was extracted with dichloromethane which was washed with saturated sodium bicarbonate, brine, and then dried with sodium sulfate. The solvent was removed in vacuo affording 1.254 g (2.82 mmol, 97%) of a white solid. Recrystallization from isopropyl alcohol afforded 0.81 g (1.82 mmol, 63%) of white crystals, mp 189°–190°: $[\alpha]_D^{23}+25.6°$ (DMF); ir (KBr) 3333, 1745, 1642, 1252 cm$^{-1}$; nmr (DMSO-d$_6$) $\delta_H$ 1.11 (t, 3 J=7, —CH$_3$), 2.97–4.77 (m, 8), 5.53 (d, 1, J=8, —HCONO$_2$), 5.72 (s, 1, —OCHO—), 5.80 (s, 1, —OCHO—), 7:40 (s, 10, aromatic); ms 445 (4.2), 444 (54.4), 443 (98.1), 398 (26.8), 107 (12.4), 106 (34.4), 105 (100.0), 91 (43.2), 77 (56.5), 51 (13.3), 44 (59.2), 43 (11.3), 40 (32.4).

Anal. Calcd for C$_{22}$H$_{23}$O$_9$N: C, 59.32; H, 5.20; N, 3.14. Found: C, 59.59; H, 5.28, N, 2.99.

EXAMPLE XVI

Ethyl 3,5:4,6-Di-O-benzylidene-2-nitrato-L-gulonate

To a 500-ml 3-neck flask was added 10.0 g (25 mmol) of ethyl 3,5:4,6-di-O-benzylidene-L-gulonate followed by 258 ml of dichloromethane. After cooling the resulting slurry to −15°, 17.2 ml of acetic anhydride was added. To a 100-ml 3-neck flask was added 27 ml of acetic anhydride. After cooling to 0°, 10.9 ml of 70% nitric acid was added dropwise maintaining the reaction temperature between −3° and 2°. The addition was complete in 45 min and the reaction mixture was allowed to warm to 7°. Under these conditions no exothermic reaction occurred. After cooling to less than 0°, this solution was added via a jacketed addition funnel cooled with methanol—ice to the acetic anhydride solution containing 3,5:4,6-di-O-benzylidene-L-gulonate. The reaction mixture was maintained at −10° to −15° during the addition. The white slurry gradually became homogeneous. After 30 min, the reaction mixture was poured onto 2 l of ice—water and mechanically stirred for 0.5 hr. This solution was extracted eight times with 100 ml of dichloromethane, then the combined organic layers were extracted two times with 300 ml of saturated sodium bicarbonate and 300 ml of brine. After drying with sodium sulfate, the solvent was removed in vacuo affording a white solid which was recrystallized from 800 ml of isopropanol. The first crop of crystals weighed 7.59 g (17.1 mmol, 68%), mp 186°–188°. An additional 1.24 g of material was obtained by concentration of the mother liquor and crystallization (2.80 mmol 11%) for a total yield of 79%.

EXAMPLE XVII

Ethyl 3,5:4,6-Di-O-benzylidene-L-xylo-hexulosonate from Ethyl 3,5:4,6-Di-O-benzylidene-2-nitrato-L-gulonate To 24 ml of diethyl ether containing 0.433 g (0.97 mmol) of ethyl 3,5:4,6-di-O-benzylidene-2-nitrato-L-gulonate at 0°–5° was added 0.14 ml (1.0 mmol) of triethylamine. This heterogeneous solution was stirred for 15 min, then 20 ml of dichloromethane was added. The resulting homogeneous solution was stirred for 5 min at 0°–5° and then worked up by adding 30 ml of dichloromethane and extracting with 25 ml of 1 N hydrochloric acid two times, 25 ml of saturated sodium bicarbonate two times, 50 ml of brine, and finally drying with sodium sulfate. Removal of the solvent in vacuo afforded 0.374 g (0.94 mmol, 97%) of the desired ketone contaminated with residual starting material. Recrystallization afforded material which was identical with that prepared in Example X.

EXAMPLE XVIII

The methods of Example XI to XVII may be repeated replacing the L-gulonates with the D-gulonates to obtain the corresponding D-xylo-hexulsonates.

EXAMPLE XIX

Ethyl 2-Keto-L-gulonate

To 15 ml of 70% acetic acid—water was added 1.19 g (3.0 mmol) of ethyl 3,5:4,6-di-O-benzylidene-L-xylo-hexulosonate. The resulting heterogeous solution was heated at 70°–75°. After 3 hrs the solution was homogeneous and was heated for an additional hr. The solvent was removed in vacuo affording a white foam, 0.574 g (2.59 mmol, 86%). This material was identical by tlc, hplc, ir, $^1$H-nmr, and $^{13}$C-nmr with an authentic sample of ethyl 2-keto-L-gulonate prepared according to the method of Drefahl and Gross.*

*G. Drefahl and B. Gross, J. Prakt. Chem., 1, 153 (1955).

This hydrolysis has also been carried out using:

water—methanol, Amberlite IR-120 sulfonic acid cation exchange resin isopropanol—water, catalytic amount of concentrated sulfuric acid acetonitrile—methanol, Dowex 50-X8 sulfonic acid cation exchange resin ethylene glycol—tetrahydrofuran, methanesulfonic acid; under these conditions ethyl 2-keto-L-gulonate was initially produced but on standing with the residual quantities of ethylene glycol and methanesulfonic acid this was converted to ascorbic acid

EXAMPLE XX

The method of Example XIX may be repeated replacing 3,5:4,6-di-O-benzylidene-L-xylo-hexulsonate with the corresponding D-xylo-hexulsonate to obtain ethyl 2-keto-D-gulonate.

What is claimed is:

1. A process for preparing 2-keto-L-gulonic acid or ester or D-enantiomers thereof which comprises
   (a) contacting D- or L-gulono-1,4-lactone with either at least two equivalents of an aldehyde dialkyl of the formula $R_2CH(OR_1)_2$ or at least two equivalents of an aldehyde of the formula $R_2CHO$ and at least one equivalent of an alcohol of the formula $R_1OH$ in the presence of an acid having a $pK_a$ less than 3 at a temperature of from about 0° to about 70° C. to obtain a compound of the formula

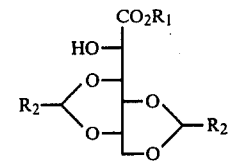

wherein $R_1$ is alkyl having 1 to 6 carbon atoms and $R_2$ is alkyl having 1 to 6 carbon atoms, phenyl or monosubstituted or disubstituted phenyl wherein said substituents are alkyl having 1 to 6 carbon atoms, alkoxy having 1 to 6 carbon atoms, chloro, bromo, fluoro or nitro, (b) oxidizing the product of step (a) with an agent which oxidizes secondary alcohols to ketones to obtain a compound of the formula

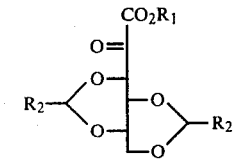

and (c) hydrolyzing the compound formed in step (b) under acid conditions at a temperature of from about 35° to 150° C.

2. The process of claim 1 wherein $R_1$ is methyl, ethyl or isopropyl.

3. The process of claim 1 wherein $R_2$ is phenyl.

4. The process of claim 1 wherein $R_2$ is methyl.

5. The process of claim 1 wherein said oxidizing agent is a sulfoxonium salt.

6. The process of claim 1 wherein said oxidizing agent is a combination of potassium periodate and ruthenium dioxide in the presence of a base.

* * * * *